(12) United States Patent
Dreher

(10) Patent No.: US 8,852,262 B2
(45) Date of Patent: Oct. 7, 2014

(54) STENT

(75) Inventor: Gael Dreher, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 255 days.

(21) Appl. No.: 13/320,252

(22) PCT Filed: May 12, 2010

(86) PCT No.: PCT/EP2010/056557
§ 371 (c)(1), (2), (4) Date: Feb. 22, 2012

(87) PCT Pub. No.: WO2010/130788
PCT Pub. Date: Nov. 18, 2010

(65) Prior Publication Data
US 2012/0143307 A1    Jun. 7, 2012

Related U.S. Application Data

(60) Provisional application No. 61/178,416, filed on May 14, 2009.

(30) Foreign Application Priority Data

May 14, 2009 (GB) .................................. 0908315.5

(51) Int. Cl.
*A61F 2/90* (2013.01)
*A61F 2/91* (2013.01)
*A61F 2/915* (2013.01)

(52) U.S. Cl.
CPC .......... *A61F 2/91* (2013.01); *A61F 2002/91583* (2013.01); *A61F 2002/91558* (2013.01); *A61F 2/915* (2013.01); *A61F 2002/91508* (2013.01)
USPC ......................................... 623/1.15; 623/1.34

(58) Field of Classification Search
None
See application file for complete search history.

(56) References Cited

U.S. PATENT DOCUMENTS

2001/0039447 A1    11/2001    Pinchasik et al.
2004/0087900 A1*    5/2004    Thompson et al. ........ 604/96.01
(Continued)

FOREIGN PATENT DOCUMENTS

EP    1129673 A2    9/2001
WO    2007035023 A1    3/2007
(Continued)

OTHER PUBLICATIONS

PCT/EP2010/056557 filed May 12, 2010 International Preliminary Report on Patentability dated Aug. 11, 2011.

(Continued)

*Primary Examiner* — Thomas J Sweet
*Assistant Examiner* — Rebecca Preston
(74) *Attorney, Agent, or Firm* — Rutan & Tucker, LLP

(57) ABSTRACT

A stent (10) formed by slitting a tube to create a matrix of struts which are separated from each other by no more than the width of the slit and which lie more or less parallel to each other and to the longitudinal axis of the tube, the slitted tube being radially expandable to a stenting disposition in which the struts exhibit a zigzag pattern in successive loops around the circumference of the stent, the angle each strut makes with the longitudinal axis increasing as the stent diameter increases the zigzag pattern exhibiting a cusp between any two adjacent struts with selected tied cusps of any one loop being connected by a bridge (12) to a facing cusp of the adjacent loop, the bridge extending in a direction parallel to the longitudinal axis of the tube and with intervening free cusps (46, 48), between any two bridge of a loop, not being connected to the adjacent loop the zigzag pattern exhibiting a lengthwise staggering of circumferentially adjacent said slits to the extent that the lengths of two circumferentially adjacent struts on the zigzag pattern that flank a tied cusp are different and further such that, in the said stenting disposition, the free cusps of adjacent loops are circumferentially displaced from each other; and characterized in that: a majority of the struts in any one of the successive loops share a first common length X, and any remaining struts in said one loop share a second common length Y (42), wherein Y<X.

12 Claims, 3 Drawing Sheets

(56) References Cited

U.S. PATENT DOCUMENTS

2007/0233235 A1* 10/2007 Chouinard .................. 623/1.15
2010/0004725 A1   1/2010 Zipse et al.
2010/0016949 A1   1/2010 Wack

FOREIGN PATENT DOCUMENTS

| WO | 2008025762 | A1 | 3/2008 |
| WO | 2008028964 | A2 | 3/2008 |
| WO | 2008119837 | A2 | 10/2008 |
| WO | 2009003584 | A1 | 1/2009 |

OTHER PUBLICATIONS

PCT/EP2010/056557 filed May 12, 2010 International Seach Report dated Aug. 9, 2010.

PCT/EP2010/056557 filed May 12, 2010 Written Opinion dated Aug. 9, 2010.

* cited by examiner

STENT

PRIORITY

This application is a U.S. national stage application under 35 USC §371 of International Application No. PCT/EP2010/056557, filed May 12, 2010, claiming priority to United Kingdom Patent Application No. 0908315.5, filed May 14, 2009, and to U.S. Provisional Application No. 61/178,416, filed May 14, 2009, each of which is incorporated by reference in its entirety into this application.

FIELD OF THE INVENTION

This invention relates to a stent formed by slitting a tube to create a matrix of struts which are separated from each other by no more than the width of the slit and which lie parallel to each other and to the longitudinal axis of the tube, the slitted tube being radially expandable to a stenting disposition in which the struts exhibit a zigzag pattern in successive loops around the circumference of the stent, the angle each strut makes with the longitudinal axis increasing as the stent diameter increases, the zigzag pattern exhibiting a cusp between any two adjacent struts, with selected tied cusps of any one loop being connected by a bridge to a facing cusp of the adjacent loop, the bridge extending in a direction parallel to the longitudinal axis of the tube, and with intervening free cusps, between any two bridge of a loop, not being connected to the adjacent loop, the zigzag pattern exhibiting a lengthwise staggering of circumferentially adjacent said slits to the extent that the lengths of two circumferentially adjacent struts on the zigzag pattern that flank a tied cusp are different and further such that, in the said stenting disposition, the free cusps of adjacent loops are circumferentially displaced from each other.

BACKGROUND ART

Self-expanding stents for the arterio-vascular system need to demonstrate a predictable and lengthy resistance to fatigue failure. Furthermore, the process used to manufacture self-expanding stents needs to be rigorous and competitive. Applicant discloses in WO 2008/119837 an attractive stent design that lends itself to manufacture by laser cutting of a tube of stent material such as nickel titanium shape memory alloy. The slits that are cut in the tube by the laser are all straight and parallel to the axis of the tube, leaving the slits cut by the laser parallel with each other so that the struts of the stent, that lie between adjacent slits, are themselves also straight and parallel with the axis of the tube (at least in the moment that they are formed). Modelling of the stress distribution in the struts of the stent matrix is therefore a task that is relatively simple, by which we mean, simple when compared with a stent matrix in which the struts are not straight or not of constant cross section.

Apart from fatigue performance, a stent design should be amenable to delivery through a tortuous bodily lumen, and then, for some applications, competent to endure severe bending, even after deployment, to follow without undue difficulty the changes of shape and configuration of the bodily lumen in which they are installed. Between adjacent struts of a zigzag turn around the stented bodily lumen, there are the "cusps" or "peaks" where two adjacent struts come together. In axially adjacent zigzag loops of the stent, after deployment, it is desirable that the peaks of the adjacent loops do not clash, "head-to-head" when the bodily lumen bends, and the stent with it. The above-mentioned WO 2008/119837 offers a stent design that, even though it is simple, achieves a configuration, upon deployment, in which the peaks of one ring face the valleys of the adjacent stenting loop, rather than its peaks. As stents are progressively installed, in ever more "bendy" lumens of the human body, there is an increasing requirement for such stents to undergo severe bending, after deployment, without that bending giving rise to any tissue damage in the stented lumen. Head-to-head clashes of cusps ought to be scrupulously avoided.

Applicant's earlier WO 01/32102 provides capacity to bend, in a simple linear strut matrix, by sacrificing part of the surface area of the cylinder to so-called "scrap portions" of the cylinder that are cut out of it and discarded, to leave significant end to end gaps between facing cusps of struts. On the inside of the bend, when the stent cylinder takes up a banana shape, the facing cusps approximate. The gap gets smaller but does not close completely. It is time-consuming and expensive to remove the scrap portions during manufacture and removing them conflicts with the objective of using the maximum possible surface area of the stent to push on bodily tissue to keep the stented bodily lumen patent.

WO2009/003584 is another publication of a self-expanding stent matrix with gaps between end to end facing cusps of co-linear struts, which therefore suffers from the same disadvantages of the stent matrices disclosed in Applicant's aforesaid WO 01/32102.

The present invention arises out of an appreciation by the present invention that the stent architectures disclosed in WO 2008/119837 are unexpectedly susceptible of further improvement. There is a further design simplification, that makes available enhanced design modelling, simpler manufacture and the chance to secure yet further improvements in stent performance after implantation.

SUMMARY OF THE INVENTION

According to the present invention there is provided a stent in the field of this invention, in which a majority of the struts in any one of the successive loops share a first common length X, and any remaining struts in said one loop share a second common length Y, wherein Y<X.

The loops of the stent can be endless, which is to say that the stent matrix exhibits a stack of endless loops arranged along a longitudinal axis of the stent, and each joined to the axially adjacent loop by one or more bridges. Alternatively, the loops of the stent can be the successive turns of a spiral that runs all the way from one end of the stent to the other. It is trite to observe that a chain is only as strong as its weakest link. With the invention, there being in the matrix no struts having a length longer than the common length X, there is present no individual strut that can pull down the performance of the struts of the strut majority. It is in this way that the difference between the stents of the present invention, and those of Applicant's earlier WO 2008/119837, can best be appreciated.

Typically, each loop of a stent exhibits one or more repeat units that are constituted by a plurality of struts of the loop. Typically, with the present invention, there is only one strut of length Y, in each such repeating unit.

The archetypal stent of the present invention exhibits struts that share a common thickness in the radial direction of the stent, and a uniform width, transverse to their length and thickness. However, stents in which the width of each strut varies, along the length of the strut, are also envisaged. One advantage of such architecture is that it can be used to optimize the distribution of stress in each one of the struts, the optimization being done by appropriate variation of the widths of the struts. Thus, for example, one might arrange for the level of stress after deployment, anywhere in the strut, to be at the same level, by providing that the struts are wider at their roots, close to a cusp of the zigzag ring, than they are along their length, midway between the respective cusps at each end of the strut in view.

It may be desirable to provide the stent with end loops, one at each end of the length of the stent, that differ from the loops intermediate the two end loops. The case is also contemplated, where the loop at one end of the stent is a special end loop, but the loop at the other end of the stent is not special. Any such special end loops might exhibit a strut length that is greater than in the intermediate loops, resulting in the axial length of such an end loop of the stent, as such, being greater than the axial length of each of the intermediate loops of the stent.

Further, it will likely be attractive to provide the stent with a plurality of radiopaque markers, likely located on one or both of the opposed ends of the stent. It might be attractive to locate the markers within the axial length of the end loop, so that they do not protrude beyond the length of the stent as such. Any such markers within the length of the stent can be asymmetric, in the sense that they are cantilevered from a cusp of the end loop of the stent, and are asymmetric about a mirror plane, parallel to the length of the stent and passing through the point where the marker is joined to the cusp of the end loop of the stent.

The radiopaque markers are intended to be readily detectable by the radiologist and so will benefit from a relatively large surface area. It will generally be attractive for this large surface area to be part of the generally cylindrical envelope in which the stent matrix is located. In other words, each radiopaque marker will preferably have opposed major surfaces that are each part-cylindrical.

For a better understanding of the present invention, and to show more clearly how: the same may be carried into effect, reference will now be made, by an example, to the accompanying drawings.

DETAILED DESCRIPTION

Figure 1:
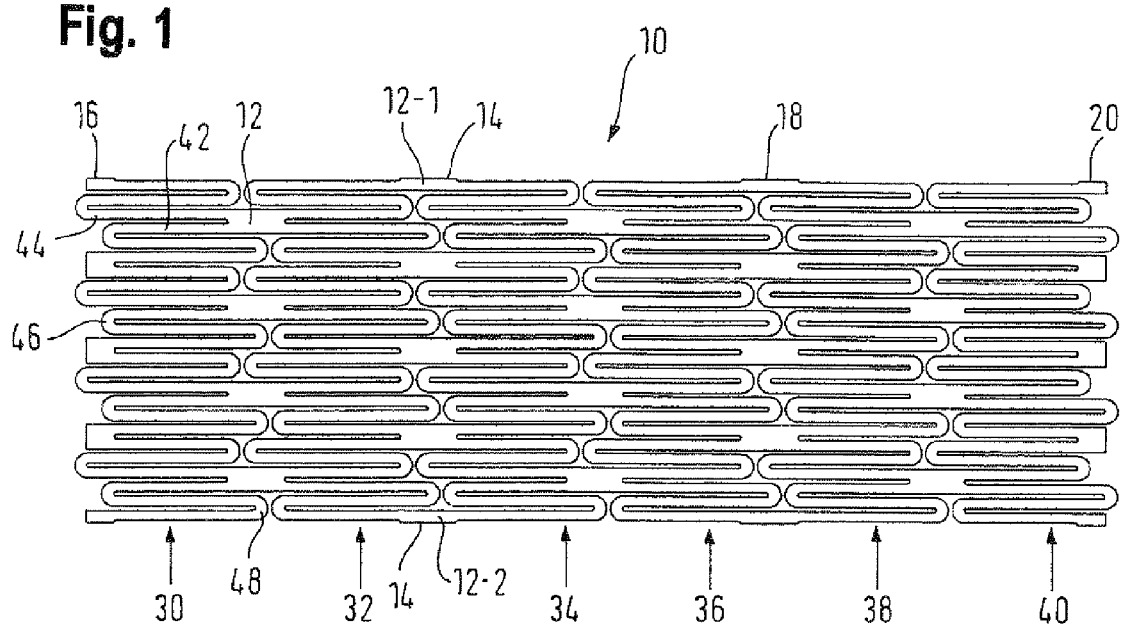
FIG. 1 is a plan view of part of a stent matrix, opened out flat.

Considering first what is shown in FIG. 1, the drawing shows a portion of the length of the stent (10), but the entirety of its circumference, yet laid out flat. The bridge (12) is parted along a notional parting line 14, that appears at both the top and the bottom of the drawing Figure, to divide the bridge (12) into a portion (12-1) on the top of the drawing and a portion (12-2) at the lower end of the drawing. Other bridges along that line of the length of the stent, (16, 18 and 20), are similarly split lengthwise notionally, for the purposes of the laid flat display in FIG. 1.

Each endless loop (30, 32, 34, 36, 38 and 40) of the stent portion shown in FIG. 1 exhibits a zigzag sequence of 24 struts, of which 8 of the struts, designated 42, have a shorter length Y than the length X of the remaining 16 struts (44). There are 12 cusps (46) at one axial end of each zigzag ring, and a further 12 cusps (48) at the other axial end of each zigzag loop. Between any two adjacent cusps of each zigzag ring, there are three struts, two of these being of length X, and one of them being shorter, strut 42, of length Y. Distributed all over the stent matrix can be seen further bridges (12) that tie together two facing cusps of two adjacent zigzag rings, and which may be designated to "bridges" to join together adjacent loops of the stent matrix, with free cusps (46), not attached to the adjacent zigzag loop, lying in between any pair of the set of four bridges that join together any particular adjacent zigzag loops of the matrix.

Figure 2:
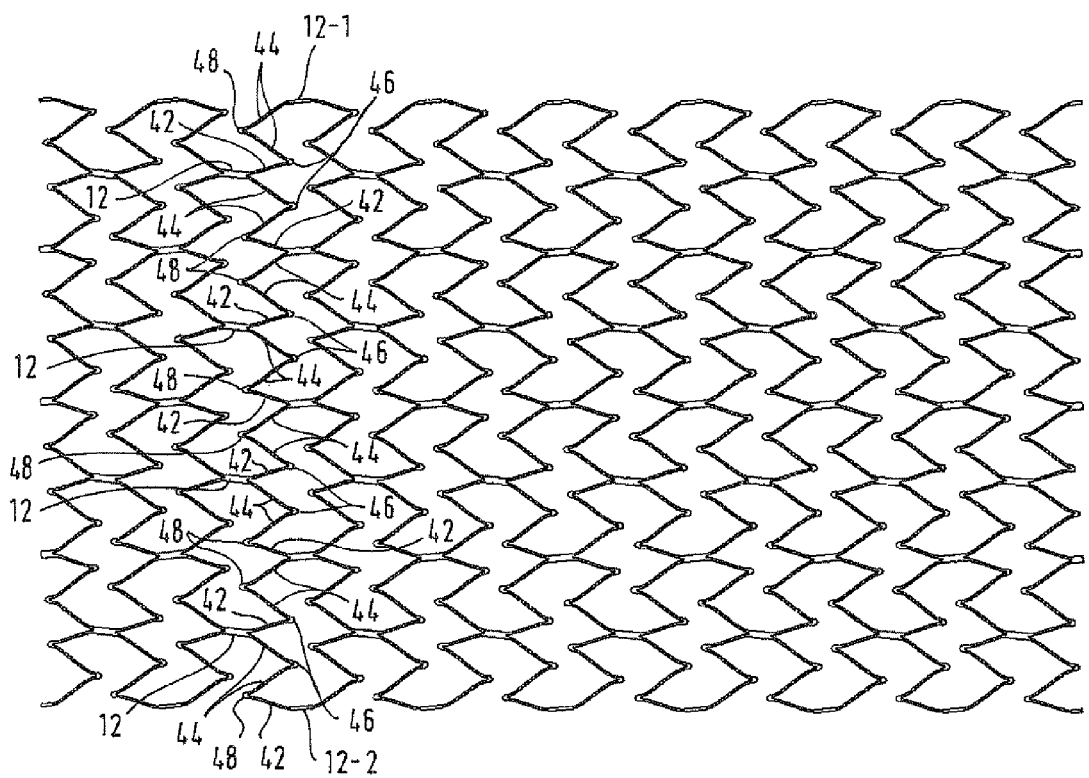
FIG. 2 is a plan view of the same matrix (but a larger portion of it) after radial expansion, but again laid flat.

As can be seen from FIG. 2, when the stent matrix of FIG. 1 is radially expanded, any free cusp of any zigzag loop lies circumferentially in the gap between two cusps of the facing axial end of the next adjacent zigzag loop of the matrix. This effect is caused by the length differential of the struts, the shorter struts Y being somewhat more resistant to bending, when the radial expansion takes place, than the slightly longer struts (44) of length Y.

Thinking about the performance in fatigue of the stent matrix shown in FIG. 2, what will characterize the fatigue life is the fatigue performance of the majority of struts (44) of length X. The shorter struts (42) enjoy a relatively favourable fatigue environment, because they can more easily carry the stress shared around the circumference of the stent, and so they are not the factor that limits the fatigue life of the matrix. Thus, calculation of the fatigue life based on the majority strut (44) will predict the fatigue performance of the stent as a whole. The matrix lacks any minority group of struts that have a poorer performance in fatigue than the strut majority.

Figure 3:
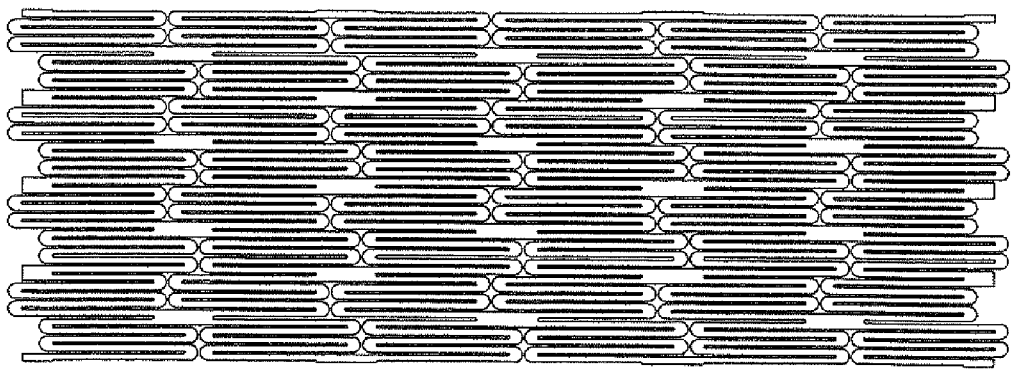
FIG. 3 is a plan view like that of FIG. 1, but of a different stent matrix.

Moving on to FIG. 3, the difference to note is that the circumference includes a greater number of lengthwise slits cut by the laser, whereby each zigzag loop of the stent matrix exhibits 40 struts rather than 24. However, each zigzag loop is connected to the axially adjacent zigzag stenting loop by a set of four bridges (12), evenly distributed around the circumference of the stent, just as in the embodiment of FIGS. 1 and 2.

Figure 6:
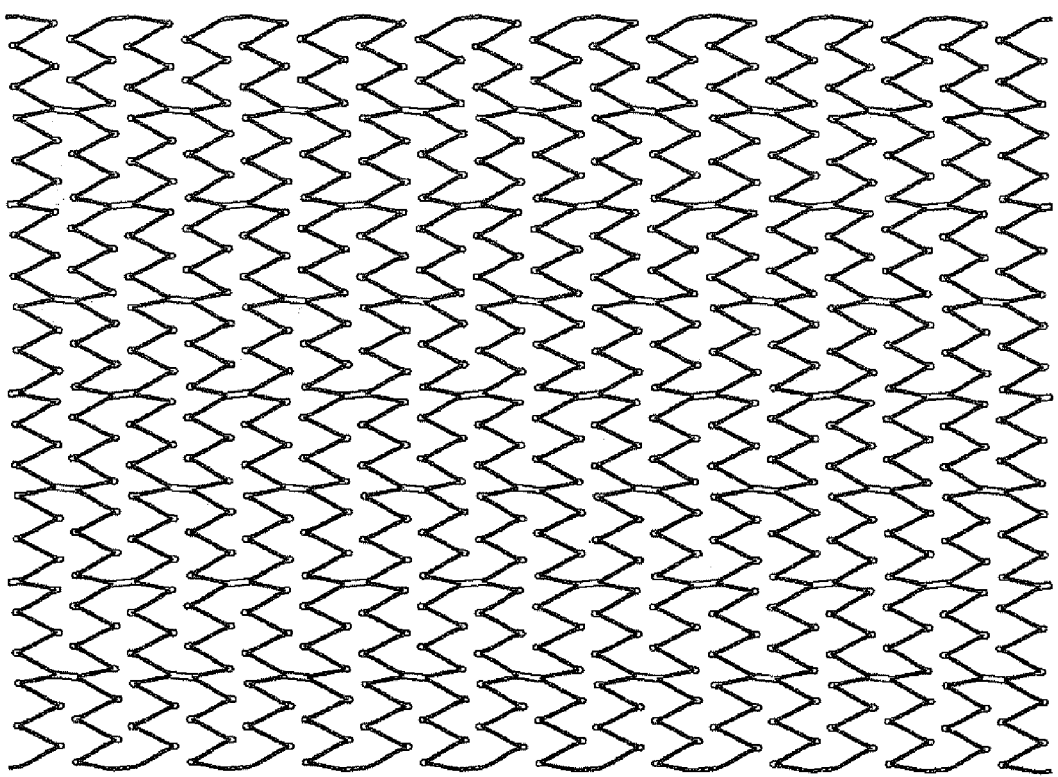
FIG. 6 is a plan view like that of FIG. 2, but showing the FIG. 3 matrix radially expanded.
Figure 7:
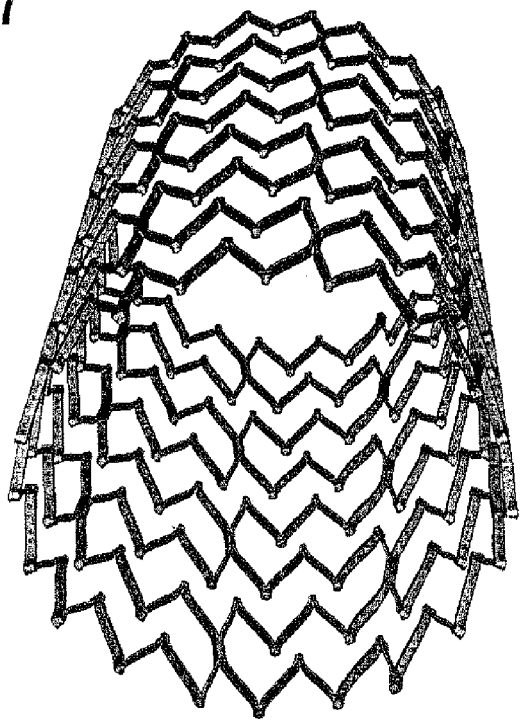
FIG. 7 shows the matrix of FIG. 6, radially expanded, but not laid flat.

FIGS. 6 and 7 show the FIG. 3 arrangement radially expanded, with FIG. 6 corresponding to FIG. 2, and FIG. 7 being useful in that it shows the stent in three dimensions whereby one can readily imagine the structure stenting surrounding bodily tissue and keeping open (patterned) the lumen inside the cylindrical stent matrix.

Figure 4:
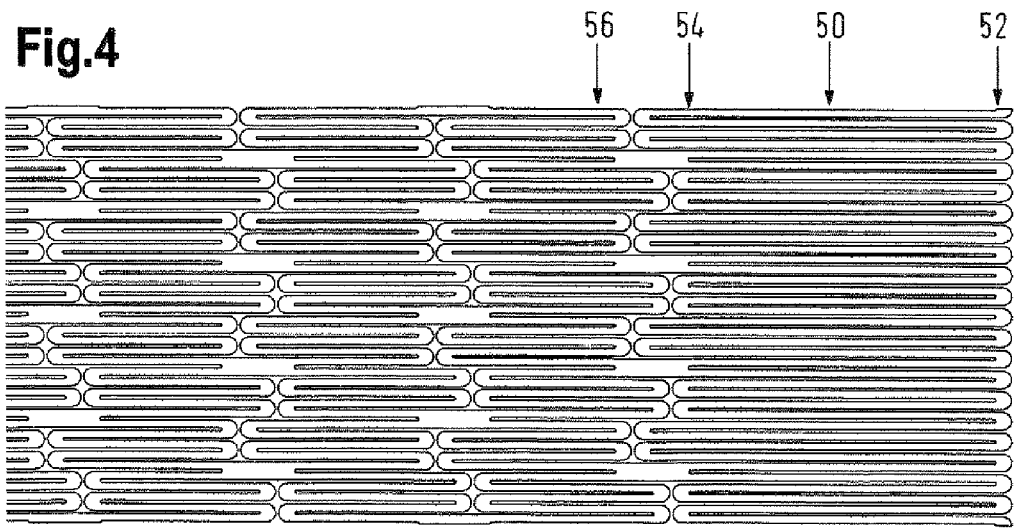
FIG. 4 is a further plan view, of an end portion of the FIG. 3 matrix.
Figure 5:
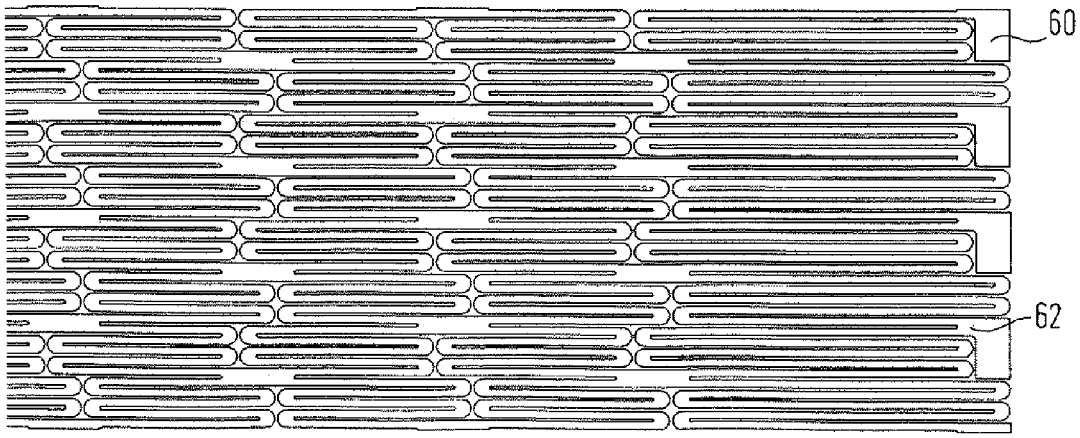
FIG. 5 is a plan view like that of FIG. 4, showing a variation with radiopaque markers.

Turning to FIGS. 4 and 5, the concern is with how to bring the stent matrix to a close, at one end of the stent cylinder. From FIG. 4, it is immediately apparent that, in the end loop (50), the axial ends of that loop differ. At the axial end (52) all cusps lie in the same plane transverse to the long axis of the stent. However, at the other axial end of the end loop (50), where it faces the next adjacent stenting loop (56), the cusps are not all in the same plane but, instead, vary in axial position in order to face, head-to-head, the cusps of the adjacent loop (56). Thus, a minority of the struts of the end loop (50) are exhibiting a longer length that the majority of struts in the end loop (50). At a stenting site, there needs to be a transition length of the bodily lumen, between the stenosis, where the stent is working at full power, and the lumen just beyond the end of the stent, where it is not pressing on the lumen wall at all. The longer struts of the end loops provide such a transition length, where the stent, thanks to the greater length of the struts, imposes less force on the lumen wall. In this way, the stresses imposed on bodily tissue by the end loop of a stent are deliberately made less than those stenting loops nearer to the center of the length of the stent, which are doing the hard job of holding open the bodily lumen in that narrowed part of its length where it was stenosed and where the stent is needed to overcome the stenosis.

Stents typically carry radiopaque markers at their ends in order that the radiologist may know with precision exactly where are the ends of the stent in relation to the length of the bodily lumen to be stented. Whereas such markers typically protrude beyond the axial length of the stent proper, FIG. 5 shows an embodiment in which the markers can be set into the length of the stent, located in circumferential gaps between spaced apart cusps in the end annulus (52) of the end ring (50).

Until now it has been typical for such radiopaque markers to be cantilevered from a cusp of a stent matrix, with the marker being symmetrical about a mirror plane that passes through the point of connection of the marker to the cusp. This need not be the case, however, as can be seen from the way in which the markers (60) in FIG. 5 are attached to a cusp (62) which is not midway along the circumferential length of the marker (60).

The present invention is not concerned with specific coatings of stents, or applications of stents. The skilled reader will not need to be told in this application what possibilities exist for covering a stent matrix with a graft material, or a medically active material, nor with what categories of bodily lumen the stent may be useful for. The skilled reader will also immediately appreciate the simplicity of the arrangements illustrated in the accompanying drawings, together with the performance characteristics evident from FIGS. 2, 6 and 7 and the opportunities evident from FIGS. 1, 3 and 5 to provide radiopaque markers as desired.

Whereas the present description is in relation to stent matrices cut by laser from a starting tube of nickel titanium shape memory alloy, the principles of this invention are equally applicable to stents made of other materials (such as stainless steel) and from flat sheet as opposed to tube stock. There is a wealth of published knowledge in the field of stent designs, and all of this knowledge is available to those skilled in the art who wish to optimise the inventive concept disclosed in the present application. However, as stent matrix design becomes more sophisticated, and as performance enhancements become ever more difficult to achieve, a contribution that can enhance performance by yet another increment, however small, is not to be underestimated, or dismissed lightly, for it is a worthwhile, and non-obvious, contribution to the art.

The archetypal stent is cylindrical when relaxed. However, the technical field of stents includes stent grafts and includes many proposals for a stent matrix which is a relaxed configuration is not strictly cylindrical. In particular, those skilled in the art are familiar with the so-called "flared" stents that exhibit at least a portion of the stent length not of constant diameter. Stents with outwardly flared ends are relatively common. All are within the scope of this invention.

The invention claimed is:

1. A stent formed by slitting a tube with a plurality of slits to create a matrix of struts wherein:
   struts of the matrix of struts lie parallel to each other and to a longitudinal axis of the tube in a delivery disposition of the stent,
   the slit tube is radially expandable to a stenting disposition in which the struts exhibit a zigzag pattern in successive loops around a circumference of the stent,
   an angle each strut makes with the longitudinal axis increases as a diameter of the stent increases,
   the zigzag pattern exhibits either a tied cusp or a free cusp between any two adjacent struts,
   each tied cusp of any one loop is connected by a bridge to a facing tied cusp of an adjacent loop,
   each bridge extends in a direction parallel to the longitudinal axis of the tube,
   free cusps located between any two tied cusps of a loop are not directly connected to the adjacent loop,
   the matrix of struts are free of significant end to end gaps between facing pairs of intervening free cusps,
   the zigzag pattern exhibits a lengthwise staggering of circumferentially adjacent slits to the extent that lengths of two circumferentially adjacent struts on the zigzag pattern that flank a tied cusp are different,
   in a stenting disposition, the free cusps of adjacent loops are circumferentially displaced from each other,
   a majority, but not all, of the struts in any one of the successive loops share a first common length X,
   all remaining struts in the one loop share a second common length Y,
   Y<X
   and
   the stent includes a plurality of radiopaque, asymmetric cantilever markers located on an annulus that lies within the length of one end loop of two end loops of the stent.

2. The stent according to claim 1, the loops being endless.

3. The stent according to claim 1, wherein a calculated fatigue life of the said remaining struts, with common length Y, exceeds a calculated fatigue life of the struts of the majority, with common length X.

4. The stent according to claim 1, in which each loop exhibits one or more repeat unit constituted by a plurality of struts of the loop, and there is only one strut of length Y, per repeat unit.

5. The stent according to claim 1, in which the struts of length X and the struts of length Y share a common thickness in a radial direction of the stent.

6. The stent according to claim 1, in which the struts of length X and the struts of length Y share a common width, transverse to a length thereof.

7. The stent according to claim 1, wherein one of the two end loops having a strut length greater than a strut length of the struts in the loops between the ends of the stent, whereby an axial length of the one of the two end loops is greater than an axial length of any loop other than the one of the two end loops of the stent.

8. The stent according to claim 1, wherein each of the markers has opposed major surfaces that are each part-cylindrical.

9. The stent according to claim 1, wherein each of the markers has a similar asymmetric shape aligned to face in a same direction.

10. The stent according to claim 1, wherein lengths of two circumferentially adjacent struts that flank at least one free cusp are the same.

11. A stent configured to expand from a delivery disposition to a stenting disposition, comprising a body including a matrix of struts formed by slitting a tube with a plurality of slits, wherein:
   in the delivery disposition adjacent struts are separated by no more than a width of one of the slits and lie parallel to a longitudinal axis of the stent,
   an angle each strut makes with the longitudinal axis of the stent increases upon radial expansion of the body from the delivery disposition to the stenting disposition, in the stenting disposition the matrix of struts exhibits a zigzag pattern in successive loops around a circumference of the stent, the zigzag pattern exhibits either a tied cusp or a free cusp between any two adjacent struts, each tied cusp of any one loop is connected by a bridge to a facing tied cusp of an adjacent loop, each bridge extending in a direction parallel to the longitudinal axis of the stent, intervening free cusps, between any two tied cusps of a loop, are not directly connected to the adjacent loop, the matrix of struts is free of significant end-to-end gaps between facing pairs of the intervening free cusps, the zigzag pattern exhibiting a lengthwise staggering of circumferentially adjacent slits, lengths of two circumferentially adjacent struts on the zigzag pattern that flank a tied cusp are different, in a stenting disposition, the free cusps of adjacent loops are circumferentially displaced from each other, a majority of the struts in any one of the successive loops share a first common length X, remaining struts in the one loop share a second common length Y, $Y<X$ and the stent includes a plurality of radiopaque, asymmetric cantilever markers located on an annulus that lies within the length of one end loop of the stent.

12. The stent according to claim 11, wherein lengths of two circumferentially adjacent struts that flank at least one free cusp are the same.

\* \* \* \* \*